(12) United States Patent
Gardner et al.

(10) Patent No.: US 7,849,727 B2
(45) Date of Patent: Dec. 14, 2010

(54) GAS-SENSING SEMICONDUCTOR DEVICES

(75) Inventors: Julian William Gardner, Kineton (GB); Florin Udrea, Cambridge (GB); Takao Iwaki, Aichi (JP); James Anthony Covington, Sutton Coldfield (GB)

(73) Assignee: University of Warwick, Warwickshire (GB)

( * ) Notice: Subject to any disclaimer, the term of this patent is extended or adjusted under 35 U.S.C. 154(b) by 305 days.

(21) Appl. No.: 12/065,296

(22) PCT Filed: Jul. 12, 2006

(86) PCT No.: PCT/GB2006/050199

§ 371 (c)(1),
(2), (4) Date: Feb. 29, 2008

(87) PCT Pub. No.: WO2007/026177

PCT Pub. Date: Mar. 8, 2007

(65) Prior Publication Data

US 2009/0126460 A1      May 21, 2009

(30) Foreign Application Priority Data

Sep. 2, 2005    (GB) .................................. 0517869.4

(51) Int. Cl.
*G01N 7/00*    (2006.01)

(52) U.S. Cl. .................................................... 73/31.06

(58) Field of Classification Search ................. 73/31.06
See application file for complete search history.

(56) References Cited

U.S. PATENT DOCUMENTS 5,892,252 A    4/1999    Hammond et al.

(Continued)

FOREIGN PATENT DOCUMENTS

EP    1 324 395 A2    7/2003

OTHER PUBLICATIONS

International Search Report for corresponding Application No. PCT/GB2006/050199 mailed Dec. 27, 2006.

(Continued)

*Primary Examiner*—Hezron Williams
*Assistant Examiner*—Rodney T Frank
(74) *Attorney, Agent, or Firm*—Renner, Otto, Boisselle & Sklar, LLP

(57) ABSTRACT

A gas-sensing semiconductor device 1' is fabricated on a silicon substrate 2' having a thin silicon dioxide insulating layer 3' in which a resistive heater 6 made of doped single crystal silicon formed simultaneously with source and drain regions of CMOS circuitry is embedded. The device 1' includes a sensing area provided with a gas-sensitive layer 9' separated from the heater 6' by an insulating layer 4'. As one of the final fabrication steps, the substrate 2' is back-etched so as to form a thin membrane in the sensing area. The heater 6' has a generally circular-shaped structure surrounding a heat spreading plate 16', and consists of two sets 20', 21' of meandering resistors having arcuate portions nested within one another and interconnected in labyrinthine form. The fabrication of the heater at the same time as the source and drain regions of CMOS circuitry is particularly advantageous in that the gas-sensing semiconductor device is produced without requiring any fabrication steps in addition to those already employed in the IC processing apart from a post-CMOS back etch and deposition of the gas-sensitive layer. The circular design is advantageous in that it is the best solution to minimise the size of the membrane at fixed power loss and heated area.

28 Claims, 3 Drawing Sheets

U.S. PATENT DOCUMENTS

2004/0075140 A1  4/2004  Baltes et al.

OTHER PUBLICATIONS

British Search Report for corresponding Application No. GB0517869.4 dated Dec. 30, 2005.

Gardner et al.; Numerical simulation of a new generation of high temperature micropower gas and odour sensors based on SOI technology; Proceedings of the SPIE; The International Society for Optical Engineering; 1999; vol. 3673; pp. 104-112; ISSN 0277 786 X.

Iwaki T. et al.; "Design and simulation of resistive SOI CMOS micro-heaters for high temperature gas sensors"; Journal of Physics: Conference Series, Institute of Physics Publishing; Bristol, GB; vol. 15; No. 1; Jan. 2005; pp. 27-32; XP020093800.

GAS-SENSING SEMICONDUCTOR DEVICES

This invention relates to gas-sensing semiconductor devices for detecting the presence and/or concentration of one or more gases.

It is known to fabricate a gas microsensor within a semiconductor device. In particular it is known to produce high-temperature metal oxide conductimetric sensors using alumina substrates and semi-manual production methods. Recently, attempts have been made to manufacture silicon versions of such sensors employing a platinum heater integrated with a thin insulating membrane of silicon dioxide or silicon nitride. Such sensors offer lower power consumption than conventional sensors when operating at temperatures of typically 300° C. to 600° C. However the nature of the materials and deposition of the metal heater layer sandwiched between the two membrane layers makes the process incompatible with integrated circuit (IC) technology. There has also been much interest in the development of MOSFET potentiometric sensors using catalytic gates, for example of palladium which run at temperatures of between 120° C. and 200° C. However such sensors will have limited application due to their inefficiency and relatively high cost.

WO98/32009 discloses a gas sensor comprising a semiconductor substrate, a thin insulating layer on one side of the substrate, and a thin semiconductor layer on top of the thin insulating layer. The sensor includes at least one sensing area in which the material of the substrate has been removed to leave a membrane formed by the thin insulating layer and the thin semiconductor layer, the or each sensing area being provided with a gas-sensitive layer and a heater for heating the gas-sensitive layer to promote gas reaction with the gas-sensitive layer. Furthermore the or each sensing area incorporates a MOSFET formed in the thin semiconductor layer and forming part of the heater and/or sensor, and the sensor provides an electrical output indicative of gas reaction with the gas-sensitive layer. However such a gas sensor can only operate at relatively low temperatures because the parasitic bipolar transistor inherent in any MOSFET structure can turn on at high temperatures. In addition, if aluminium is employed as the CMOS metal layers, there is a maximum temperature of 250° C. beyond which long term degradation by either electromigration or stress can occur.

There is a need to make small, low-cost gas sensing devices that incorporate a micro-heater to elevate the temperature of a gas-sensitive layer (e.g. tin dioxide) and have integrated electronic circuitry. Gardner J. W., Pike A., de Rooij N. F., Koudelka-Hep M., Clerc P. A., Hierlemann A. and Gopel W., 1995 Sensors and Actuators, B 26 135-139, "Integrated chemical sensor array for detecting organic solvents" have reported the use of platinum or doped polysilicon to form a resistive track. However, platinum is a material that is not compatible with CMOS technology, and polysilicon requires additional process steps and forms heaters that tend to lack long-term stability. Gardner J. W., Udrea F., and Milne B., 1999 SPIE Vol. 3673 104-112, "Numerical simulation of a new generation of high-temperature, micropower gas and odour sensors based on SOI technology" proposes use of a MOSFET structure fabricated in SOI technology to form a gas sensor and integral heater. WO98/32009 also discloses the use of a MOSFET to form an active heater but, in silicon technology, the operating temperature of the device is limited to about 300 to 350° C. (see Udrea F., Gardner J. W., Setiadi D., Covington J. A., Dogaru T., Lu C-C. and Milne W. I., 2001 Sensors and Actuators, B 78 180-190, "Design and simulations of a new class of SOI CMOS micro hot-plate gas sensors") and so is unsuited for, say, methane detection that requires an operating temperature of about 550° C.

It is an object of the invention to provide an improved high-temperature gas-sensing semiconductor device which can be produced at low cost using conventional bulk fabrication processes.

According to the present invention there is provided an integrated circuit comprising a gas-sensing semiconductor device and an electronic circuit adjacent to the gas-sensing semiconductor device containing at least one MOS transistor having source and drain regions, the gas-sensing semiconductor device comprising an insulating membrane, made of silicon dioxide, silicon nitride, silicon oxynitride or a combination of silicon dioxide and silicon nitride for example, a sensing area provided with a gas-sensitive layer above the membrane and a heater embedded in the membrane for heating the gas-sensitive layer to promote gas reaction with the gas-sensitive layer, wherein the heater is made of highly doped single crystal silicon and is fabricated simultaneously with the source and drain regions of the or each MOS transistor of the electronic circuit.

Preferably the integrated circuit is made utilising CMOS Bi-CMOS, CMOS or Bi-CMOS compatible technology.

Preferably the integrated circuit is made utilising Silicon-on-Insulator (SOI) CMOS or Bi-CMOS technology The fabrication of the heater at the same time as the source and drain region of at least one MOS transistor in the adjacent electronic circuit is particularly advantageous in that the gas-sensing semiconductor device is produced without requiring any fabrication steps in addition to those already employed in the IC processing apart from a post-CMOS back etch and deposition of the gas-sensitive layer. In addition, within the integrated circuit, the gas-sensing semiconductor device may be driven and its signal processed by analogue, digital or mix-signal electronics. The control may be achieved using for example a microcontroller unit, and a current drive unit may be used to drive the heater.

The gas-sensing semiconductor device may be a resistive gas sensor or a calorimetric gas sensor. This device may also be used as a thermal sensor such as a flow sensor and thermometer without a gas-sensitive layer.

Furthermore, the use of single crystal silicon as the heater material is particularly advantageous in that it permits operation of the device at temperatures of up to 600° C., e.g. as a metal oxide (such as tin dioxide, tungsten oxide and vanadium oxide) resistive gas sensor or palladium-based calorimeter, with integrated CMOS circuitry, which can be operated at only less than 250° C. This is because the associated circuitry is thermally isolated from the heater by a thin membrane structure. It also enables high-temperature gas-sensitive materials to be applied during fabrication, such as CNT (carbon nanotube) deposition (at say 700° C.), and high-temperature annealing steps aimed at providing better long term stability.

Both membrane and outer regions of the heater may have a curved shape. This design of membrane and heater is particularly advantageous in that the curved outline provides thermal stability and limits heat dissipation, and thus enables the size of the membrane to be minimised as far as possible for a given die size. In most cases the use of a circular heater is the best solution to minimise the size of the membrane at fixed power loss because a circle has least circumference relative to any other shape of the same area. The use of a shape that does not include corners for the heater will remove regions of higher mechanical stress and so imparts a higher degree of reliability. The actual size of the substrate on which the device is fabricated dictates cost, and it is therefore advantageous that such a design enables the size to be minimised.

In a preferred embodiment of the invention the heater has a generally circular shape and comprises arcuate resistors. Advantageously the resistors have arcuate portions nested within one another and interconnected in labyrinthine form. Furthermore the heater may surround a heat spreading plate made of single crystal silicon. Furthermore a metal (e.g. tungsten, aluminium, copper) or polysilicon plate may be formed above the silicon resistive heater. The use of a heat spreading plate leads to better temperature uniformity and thus lower power consumption.

In addition to the resistive heater made of doped single crystal silicon used for the source or drain of the or each MOS transistor, four types of track structure are possible, namely a straight track made of metal, a sector shaped track of least width in the inner region, a sector shaped track of least width in the outer region, and a composite track comprising an inner part made of a semiconductor and an outer part made of a metal.

A straight track made of metal (e.g. tungsten, aluminium, copper) has a much lower resistance than the one made of semiconductor and thus generates less unwanted Joule heat in the tracks. Thus this metal track structure leads to lower power consumption than a heater with a semiconductor track.

A sector shaped track of least width in the inner region generates more heat in the inner region of the track and so can be used more efficiently to raise the temperature of the heater area. This track may be made of single crystal silicon, polysilicon or metal. Furthermore, by keeping overall width of the heater larger than the track width, larger area may be used as gas sensor, which leads to larger signal.

A sector shaped track of least width in the outer region is also advantageous in that it has lower current density in the inner region where electromigration is more likely to occur (especially if the track is made of aluminium) because of a higher temperature than the outer region. This track may be made of single crystal silicon, polysilicon or metal. Furthermore, by keeping the overall width of the heater larger than the track width, a larger area may be used for the gas sensor and this leads to larger signals.

A composite track comprising an inner region made of a semiconductor and an outer region made of a metal is also advantageous in that it has more stable material in the inner region where electromigration is more likely to occur. The outer region, where the temperature is lower than in the inner region and electromigration is less likely to occur, is made of metal which has a lower sheet resistance and thus leads to lower power consumption.

SOI technology is commonly based on wafer bonding or implantation of oxygen deep into the substrate followed by epitaxial growth (known as SIMOX techniques). Other techniques such as smart-cut can also be employed. CMOS SOI integrated circuits can be fabricated by forming various transistors into the top semiconductor layer which is isolated from the substrate through a buried silicon dioxide. Other insulating materials can be used in place of silicon dioxide, such as silicon nitride or a combination of silicon dioxide and silicon nitride. Individual semiconductor devices, such as MOSFET's, can then fabricated within the thin silicon layer using known fabrication steps. Because the electronic devices are formed within a very thin active semiconductor layer, of 0.1 to 1 µm thickness for example, SOI technology results in high speed/low power CMOS performance, as well as providing simple and efficient device isolation, reduced parasitic capacitances, latch-up elimination and reduced short-channel effects. In addition fully depleted devices (with an ultra-thin SOI layer) have been reported to have attractive features. They do not exhibit kink phenomena, have a sharp sub-threshold slope, and are stable in terms of dynamic floating body effects relating to impact-ionisation and charge-pumping phenomena. The SOI transistors also possess a lower off-state leakage current by a factor of about 10 to 100 when compared with conventional bulk silicon devices. This is important in reducing the stand-by power dissipation. In addition SOI technology enables device operation at higher temperatures than conventional devices, mainly due to reduced leakage currents.

The invention also provides a gas-sensing semiconductor device comprising a semiconductor substrate, at least one sensing area provided with a gas-sensitive layer and a heater for heating the gas-sensitive layer to promote gas reaction with the gas-sensitive layer, wherein conductive tracks are connected to the heater that taper in a direction towards the heater down to a width that is less than an overall width of the heater.

The invention also provides a gas-sensing semiconductor device comprising a semiconductor substrate, at least one sensing area provided with a gas-sensitive layer and a heater for heating the gas-sensitive layer to promote the reaction of a gas with the gas-sensitive layer, wherein conductive tracks are connected to the heater that taper in a direction away from the heater down to a width that is less than an overall width of the heater.

In order that the invention may be more fully understood, several embodiments of the invention will now be described, by way of example, with reference to the accompanying drawings, in which.

The embodiments of gas-sensing semiconductor device in accordance with the invention to be described with reference to the drawings are fabricated utilising non-SOI (e.g. bulk or epi) or SOI (e.g. Smart Cut UNIBOND) CMOS technologies in order to provide gas sensing areas integrated with IC control circuitry in a single chip, each sensing area being a thin membrane formed by at least one thin insulating layer, a doped single crystal silicon layer acting as a resistive heater and a metal (e.g. aluminium, tungsten or copper) layer acting as a resistive track. The structures in these embodiments can operate at temperatures well over 600° C. in the sensing area. The thin insulating layer, which provides thermal isolation, may be silicon dioxide, silicon nitride, a combination of silicon dioxide and silicon nitride or some other insulating material. Unlike in conventional gas microsensors, there is no need for low-stress special layer deposition involving an expensive and difficult fabrication processes. Particular attention is drawn in the accompanying description to the fabrication of the device in the sensing areas, although it will be understood that IC fabrication will be effected simultaneously to provide the associated control circuitry in other areas of the device.

Figure 1:
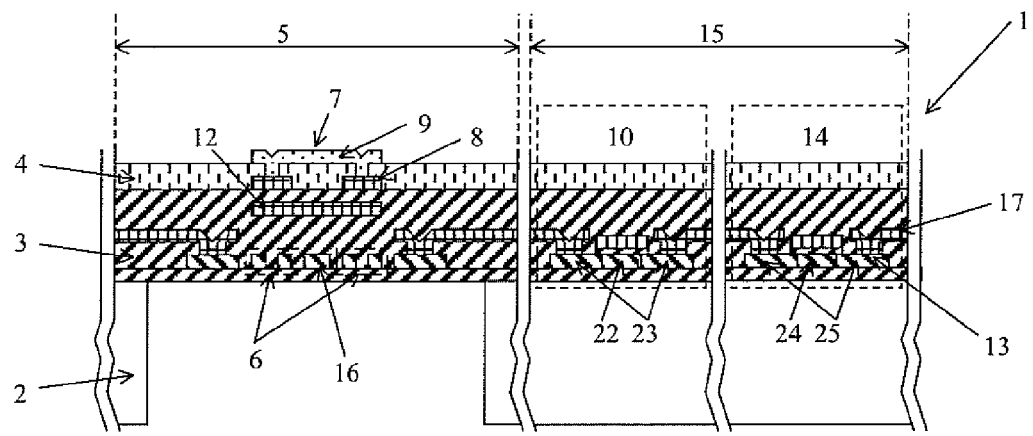
FIG. 1 is a section through sensing and control areas of a first embodiment of the invention.
Figure 2:
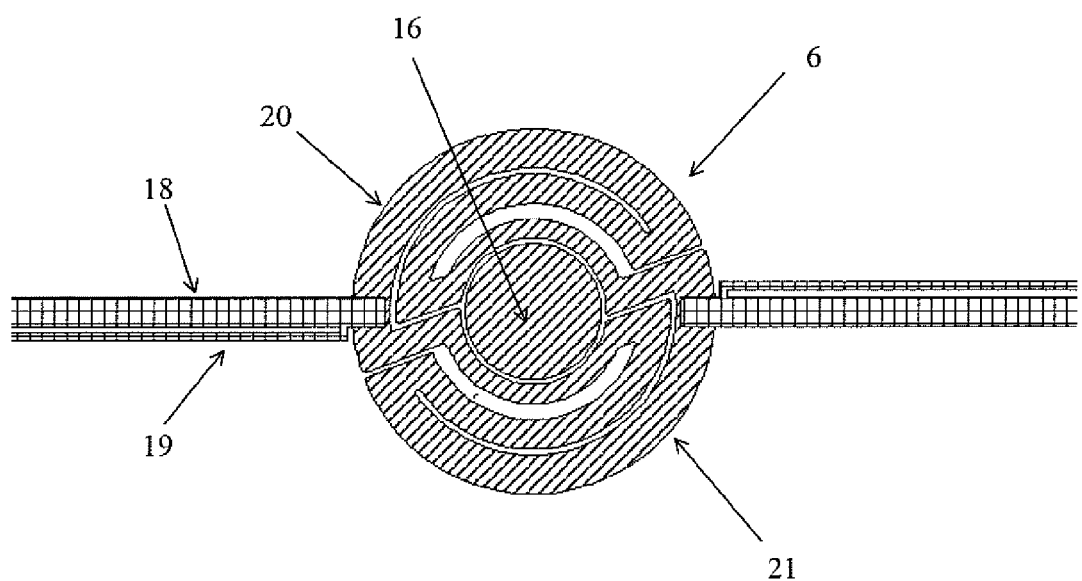
FIG. 2 is a plan view of the sensing area of the first embodiment of the invention.

In the embodiment of FIGS. 1 and 2 the device 1 is fabricated on a silicon substrate 2 having a thin silicon dioxide layer 3 on one surface, and a thin silicon nitride insulating layer 4 on top of the silicon dioxide layer 3. The thermal oxide has a much lower thermal conductivity than the silicon and therefore the thermal power losses in the sensing area 5 will be greatly reduced. A resistive heater 6 made of doped single crystal silicon is formed in the sensing area 5. This heater 6 is formed simultaneously with the source and drain regions of the associated circuitry within the CMOS process (and not as part of a post CMOS process). Thus the heater 6 in the sensing area 5 and the source and drain regions 13 in the electronic IC area 15 can be simultaneously formed from the same single crystal silicon layer, which is patterned by photolithography and isolated by trench etching to define the individual structures.

In addition to the heater 6, a chemoresistor sensor 7 is fabricated in the sensing area 5 by placing a gas-sensitive layer 9, made either of an inorganic material (such as tin dioxide) or an organic material (such as a polymer or phthalocyanine), so as to span two electrodes 8. The gas-sensitive layer 9 can be deposited by sputtering etc. or can be electrochemically grown onto the two electrodes 8 (as in the case of conducting polymers). The two electrodes 8 can be formed from a third metal layer using one of the upper metals formed as part of the CMOS metallisation, or can be of a different material such as gold and be deposited post-CMOS. Alternatively the electrodes 8 can be formed from a combination of several layers, partly within the CMOS process and partly by post-CMOS processing.

As one of the final steps in the fabrication process the substrate 2 is back-etched so as to form a thin membrane in the sensing area 5, with the silicon dioxide layer 3 serving to stop the back-etching, so that the silicon dioxide layer 3 is exposed on the opposite surface of the membrane to the silicon nitride insulating layer 4. The back-etching can be effected either by wet etching (e.g. KOH etching) or by dry etching (e.g. deep reactive ion etching).

In the electronic IC area 15, the devices are formed using the known CMOS processing. There are several CMOS or Bi-CMOS processes available, using n-tub, p-tub, twin-tub or SOI technologies. The isolation, the geometry and composition of some layers and the order of the processing steps are different from one process to another but they all incorporate major common implantation and drive-in steps, formation of gate oxides, polysilicon (one or more layers) deposition, and formation of one or several layers of metal to contact the transistor terminals and form the interconnects within the IC.

Referring to FIG. 1 a silicon dioxide layer is grown at the surface to form the gate oxide of an NMOS transistor 10 and a PMOS transistor 14 followed by the deposition and patterning of a polysilicon layer on top of the gate oxide. The n+ source and n+ drain 23 of the NMOS transistor 10 are further implanted and self-aligned to the gate, and the p+ source and p+ drain 25 of the PMOS transistor 14 are further implanted and self-aligned to the gate. Whichever type of transistor is produced a tungsten metallization layer 17 is applied and patterned on top of the source and drain diffusions.

As already mentioned the doped silicon layer 13 is also used to produce the resistive heater 6 in the membrane area. This doping process is normally performed by ion implantation of impurities, such as boron, phosphorous, arsenic and antimony, followed by annealing aimed at electrical activation of the dopants. It may also be performed by thermal diffusion of the dopants. The first metal layer, including the metallization tracks 17', is subsequently formed for interconnect purposes and isolated from other layers by interdielectric layers, commonly made of silicon dioxide. A final passivation layer, made of silicon dioxide, silicon nitride, silicon oxynitride, glass or organic material such as SU8, is formed on top of the integrated circuit, covering the whole of the IC, except the pads which contain at least a top metal layer and preferably a stack of metal layers.

When current or voltage is supplied to the heater 6, the sensing area heats up rapidly due to the high thermal insulation in the sensing area and very low thermal capacitances, thus allowing gas molecules to react with the gas-sensitive layer 9 of the sensor 7. The heater 6 can be operated in open loop control applying a constant voltage or constant current. However, by monitoring the heater resistance, it is possible to modify the heater current or voltage in a closed loop control system. This permits very accurate setting of the heater temperature and hence the temperature of the gas-sensitive layer 9. When the gas interacts with the gas-sensitive layer 9, the conductivity of the gas-sensitive layer 9 changes, and this can be detected by appropriate detection circuitry (not shown). The temperature can be monitored by detecting the change in the heater resistance with respect to a reference at room temperature.

A spreading plate 12 in the form of a second tungsten layer above the heater 6 serves to spread the heat generated by the heater 6 and to direct it towards the gas-sensitive layer 9. The electrodes 8, which may be in the form of interdigitated electrodes, underlying the gas-sensitive layer 9 are used to measure the conductance or resistance of the gas-sensitive layer 9 that is related to the concentration of the gas being analysed.

In order to monitor the temperature in the sensing area, a CMOS or Bi-CMOS integrated temperature sensor (not shown) can be fabricated in the sensing area adjacent to the gas-sensitive layer 9. Such a temperature sensor may be a passive sensor made of metal, polysilicon or silicon resistors or an active sensor made of unipolar or bipolar devices formed within the CMOS processing and may make use of variation of resistivity, the carrier mobility or the emitter-base voltage with temperature. Such temperature sensors are widely used and give accurate results.

The heater 6 has a generally circular-shaped structure and surrounds a further heat spreading plate 16 made of single crystal silicon, as shown more particularly in the plan view of FIG. 2 which further shows a conductive track 18 connected to each end of the heater 6 for the heating current supplied to the heater 6, and a further conductive track 19 connected to each end of the heater 6 for the sensing signal indicative of the temperature of the heater 6. The heater 6 itself consists of two sets 20, 21 of meandering resistors with implanted n+ and p+ doping having arcuate portions nested within one another and interconnected in labyrinthine form. The circular design is particularly advantageous in that the circular outline is a naturally isothermal shape and is the optimal shape for the heater 6 where the membrane is itself circular. More particularly the use of a circular heater (with annular spacings between the arcuate sections to convolute heat loss) is the best solution to minimise the size of the membrane at fixed power loss and gas-sensing area. In addition the removal of corners of the heater and membrane inherent in the use of such a shape will remove areas of higher mechanical stress and so provides an optimum design from the point of view reliability. The actual size of the silicon die on which the device is fabricated dictates cost, and it is therefore advantageous that such a design enables the size to be decreased. If the die can be reduced in area by 20%, then the cost to manufacture the device in volume is decreased by about 20%.

Due to the high thermal isolation properties of the membrane, high temperatures can be developed with very low electrical power consumption, and this is particularly advantageous in applications in which high temperatures are required for the gas to react with the active material of the gas-sensitive layer. The nature and concentration of different gases or of a mixture of gases can be determined by measuring the change in conductance of the gas-sensitive layer at different temperatures. Organic and catalytic-metal gas-sensitive layers may react at low temperatures (less than 100° C.) or medium temperatures (100° C. to 200° C.) whereas metal oxide gas-sensitive layers may require temperatures in excess of 200° C., and catalytic oxides may require temperatures in excess of 500° C. Thus a gas microsensor array device can be built by integrating several individual sensor cells utilising different gas-sensitive layers in the same chip. The individual sensor cells can be built on the same membrane or can have separate membranes. Such a microsensor array device possesses the advantages over individual sensors of improved gas selectivity, lower noise and reduced effect of poisoning through superior structural design or signal processing.

Figure 3:
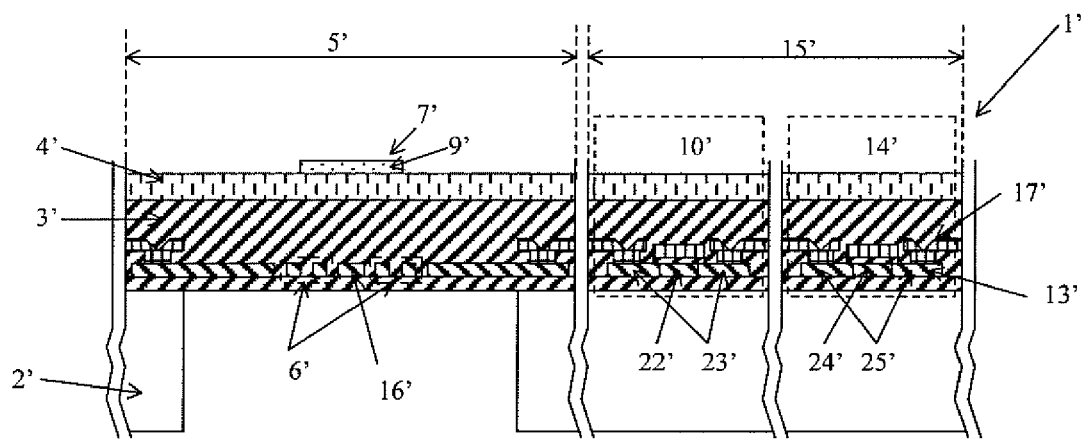
FIG. 3 is a section through a sensing area of a second embodiment of the invention.
Figure 4:
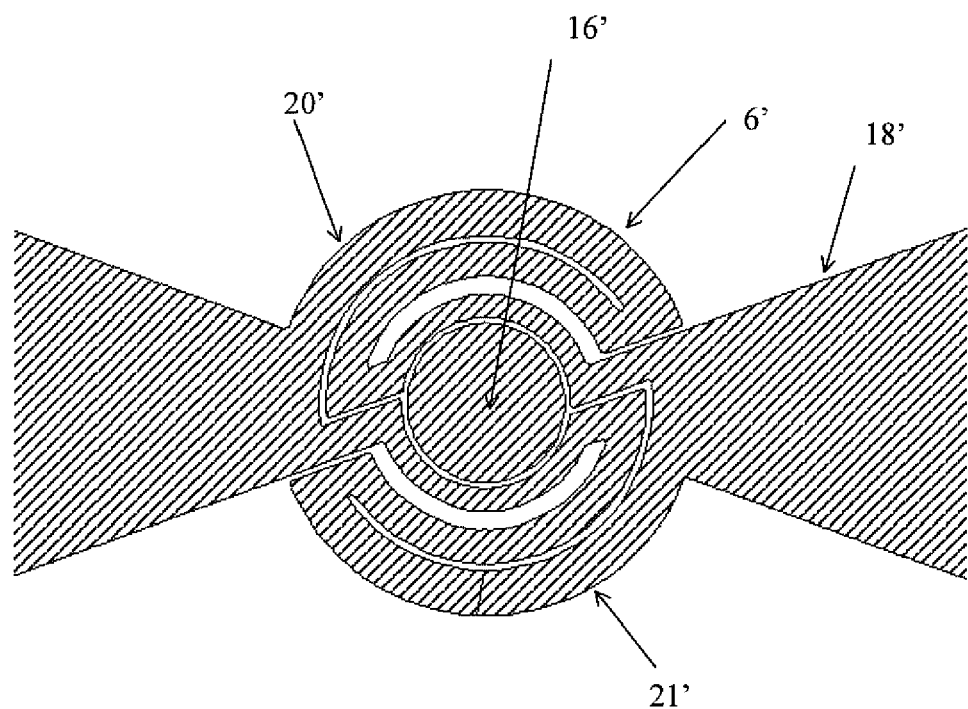
FIG. 4 is a plan view of the sensing area of the second embodiment of the invention.

The embodiment of FIGS. 3 and 4 is generally similar to the embodiment of FIGS. 1 and 2 except that the adjacent tracks are not made of metal but of doped silicon, which is formed simultaneously with resistive heater, source and drain and isolated by trench etching simultaneously with FETs. Like reference numerals primed are used in FIGS. 3 and 4 to denote the same parts as in FIGS. 1 and 2. As in the first embodiment the device 1' is fabricated on a silicon substrate 2' having a thin silicon dioxide layer 3' on one surface, and a thin silicon nitride insulating layer 4' on top of the silicon dioxide layer 3'. A resistive heater 6' is formed in the sensing area, and a chemoresistor sensor 7' is fabricated in the sensing area in the form of a gas-sensitive layer 9' spanning two electrodes (not shown).

In this case, however, as shown in the plan view of FIG. 4, the circular-shaped heater 6' surrounding the heat spreading plate 16' is connected at each end to a tapering conductive track 18' for the heating current supplied to the heater 6'. Although not shown in FIG. 4, further conductive tracks similar to those shown in FIG. 2 may be connected to each end of the heater 6' for the sensing signal indicative of the temperature of the heater 6'. As before the heater 6' itself consists of two sets 20', 21' of meandering arcuate tracks with implanted n+ and p+ doping. This doping process is normally performed by ion implantation of impurities, such as boron, phosphorous, arsenic and antimony, followed by annealing for electrical activation of the dopants. It may also be performed by thermal diffusion of the dopants. The heater 6' is connected to adjacent electronic components (not shown) by metallization tracks 17' of aluminium, tungsten or copper.

It is an important feature of such an embodiment that each of the conductive tracks 18' connected to the heater 6' tapers in the direction towards the heater 6' as a result of the fact that the doped silicon from which the tracks 18' are formed exhibits relatively high thermal conductivity and high electrical resistivity. Ideally the tracks 18' should be relatively thin in order to minimise the heat loss down the tracks 18' and relatively thick in order to minimise the power generated in the tracks 18'. As a compromise the tracks 18' are tapered so as to be relatively thin in the immediate vicinity of the heater 6' and relatively thick further away from the heater 6'. Such a tapering design is not necessary when metal tracks to a silicon heater are employed. The heat spreading plate 16' is made of silicon and it is more advantageous if there is additional metal (e.g. aluminium, tungsten and copper) heat spreading plate as this would lead to further temperature uniformity.

Instead of a resistive gas sensor, a calorimetric gas sensor may be provided with a similar structure except that the heater or a temperature sensor is used to measure the rise or fall in temperature of the gas-sensitive layer. In some cases it may be necessary to provide a metal plate on which the gas-sensitive material may be deposited electrochemically. However this is not normally necessary as the gas-sensitive layer may be deposited by sputtering, electroless plating, physical or chemical vapour deposition, etc.

The above structures can also be used as microcalorimeters (or as both chemoresistors and microcalorimeters) in which the additional heat liberated or absorbed by the gas-sensitive layer in the presence of the gas is detected. In this case, the temperature of the sensing material changes as a result of its reaction with the gas so that the nature of the gas and/or its concentration can be determined by monitoring the heat liberated or absorbed by the gas-sensitive layer in the presence of the gas. An appropriate gas-sensitive layer for such an application would be a non-electrically conducting material such as palladium doped alumina (e.g. a pellistor). Chemoresistive materials such as tin dioxide change their thermal conductivity so that it is possible to monitor the change in thermal conductivity, the heat liberated and the change in the electrical conductivity at high temperatures.

Figure 5:
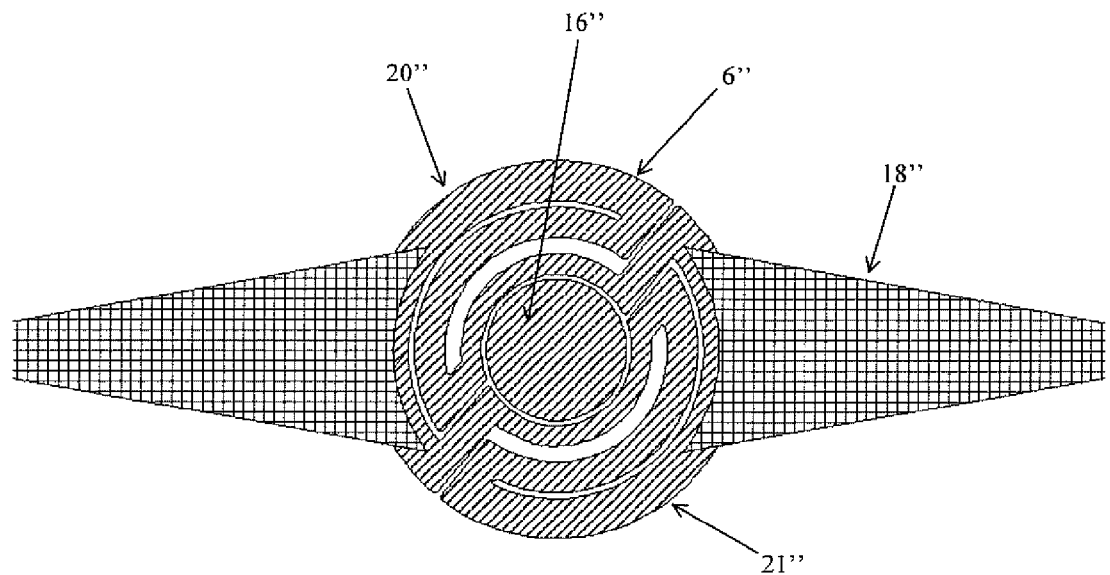
FIG. 5 is a plan view of the sensing area of a third embodiment of the invention.

The embodiment of FIG. 5 is generally similar to the embodiment of FIGS. 1 and 2 except that each of the conductive tracks 18" connected to the heater 6" tapers in the direction away from the heater. Like reference numerals are used in FIG. 5 to denote the same parts as in FIGS. 1 and 2. As in the first embodiment the device is fabricated on a silicon substrate having a thin silicon dioxide layer on one surface, and a thin silicon nitride insulating layer on top of the silicon dioxide layer. A resistive heater 6" is formed in the sensing area, and a chemoresistor sensor is fabricated in the sensing area in the form of a gas-sensitive layer spanning two electrodes (not shown).

In this case, however, the circular-shaped heater 6" surrounding the heat spreading plate 16" is connected at each end to a tapering conductive track 18", which has less width in the outer region, for the heating current supplied to the heater 6". Although not shown in FIG. 5, further conductive tracks similar to those shown in FIG. 2 may be connected to each end of the heater 6" for the sensing signal indicative of the temperature of the heater 6". As before the heater 6" itself consists of two sets 20", 21" of meandering arcuate tracks with implanted n+ or p+ doping. The heater 6" is connected to adjacent electronic components (not shown) by metallization tracks of aluminium, tungsten or copper.

It is an important feature of such an embodiment that each of the conductive tracks 18" connected to the heater 6" tapers in the direction towards the outer region of the membrane (so that the outer region of track has less width) as a result of the fact that the inner region of the membrane is heated to a higher temperature and thus electromigration is more likely to occur in the inner region. This track structure leads to less current density in the inner region and will make the track more stable against electromigration. These conductive tracks 18" may be made of metal (e.g. tungsten, aluminium and copper) or semiconductor (e.g. polysilicon or single crystal silicon).

Figure 6:
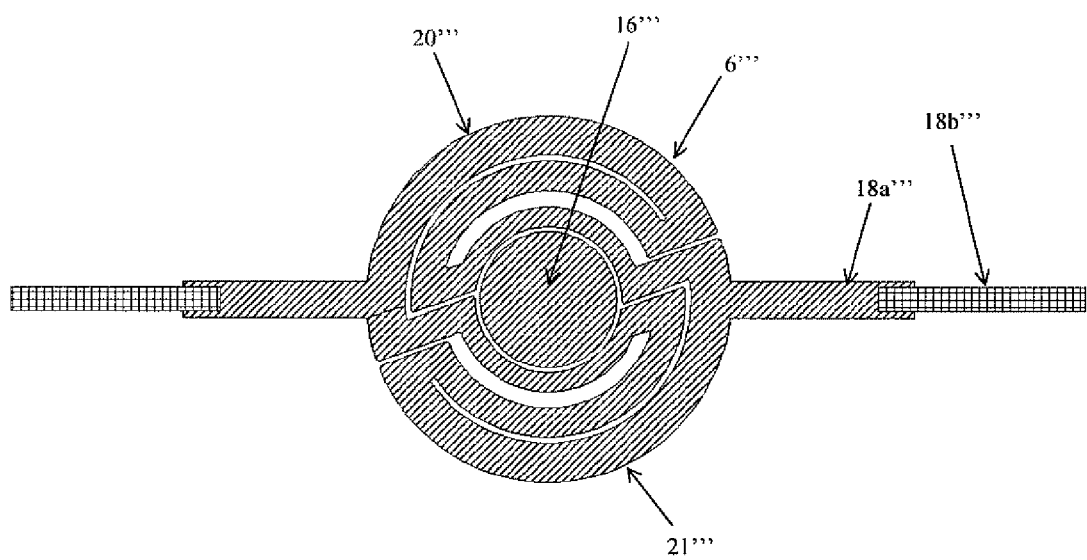
FIG. 6 is a plan view of the sensing area of a fourth embodiment of the invention.

The embodiment of FIG. 6 is generally similar to the embodiment of FIGS. 1 and 2 except that each of the conductive tracks connected to the heater 6''' comprises two parts 18a''', 18b''' made of two different materials. Like reference numerals primed are used in FIG. 6 to denote the same parts as in FIGS. 1 and 2. As in the first embodiment the device is fabricated on a silicon substrate having a thin silicon dioxide layer on one surface, and a thin silicon nitride insulating layer on top of the silicon dioxide layer. A resistive heater 6''' is formed in the sensing area, and a chemoresistor sensor is fabricated in the sensing area in the form of a gas-sensitive layer spanning two electrodes (not shown).

In this case, however, the circular-shaped heater 6''' surrounding the heat spreading plate 16'' is connected at each end to a track made of two materials for the heating current supplied to the heater 6''', the inner part 18a''' being made of a semiconductor, such as polysilicon and single crystal silicon, and the outer part 18b''' being made of a metal, such as aluminium and tungsten. Although not shown in FIG. 6, further conductive tracks similar to those shown in FIG. 2 may be connected to each end of the heater 6''' for the sensing signal indicative of the temperature of the heater 6'''. As before the heater 6''' itself consists of two sets 20''', 21''' of meandering arcuate tracks with implanted n+ or p+ doping. The heater 6''' is connected to adjacent electronic components (not shown) by metallization tracks of aluminium, tungsten or copper.

It is an important feature of such an embodiment that the inner part 18a''' of the track is made of a semiconductor that suffers less from electromigration at the high temperatures that are generated in the vicinity of the inner part and tend to generally increase the possibility of electromigration. It is also advantageous that the outer part 18b''' of the track is made of a metal which leads to lower power consumption because of its lower resistivity. This composite track structure may also be tapered as shown in FIGS. 4 and 5, which is advantageous for the reasons mentioned above.

The invention claimed is:

1. An integrated circuit comprising a gas-sensing semiconductor device and an electronic circuit adjacent to the gas-sensing semiconductor device containing at least one MOS transistor having source and drain regions, the gas-sensing semiconductor device comprising an insulating membrane, a sensing area provided with a gas-sensitive layer above the membrane and a heater embedded in the membrane for heating the gas-sensitive layer to promote gas reaction with the gas-sensitive layer, wherein the heater is made of highly doped single crystal silicon and is fabricated simultaneously with the source and drain regions of the or each MOS transistor of the electronic circuit.

2. A device according to claim 1, wherein the integrated circuit is made utilising CMOS Bi-CMOS, CMOS or Bi-CMOS processing steps.

3. A device according to claim 1, wherein the integrated circuit is made utilising SOI CMOS or SOI Bi-CMOS processing steps.

4. A device according to claim 1, wherein the heater is isolated by trench etching from the or each MOSFET.

5. A device according to claim 1, wherein the heater has a generally circular shape.

6. A device according to claim 1, wherein the membrane has a generally circular shape.

7. A device according to claim 1, wherein the heater comprises arcuate resistors.

8. A device according to claim 1, wherein the resistors have arcuate portions nested within one another and interconnected in labyrinthine form.

9. A device according to claim 1, wherein conductive tracks made of metal are connected to the heater.

10. A device according to claim 9, wherein the conductive tracks are made of tungsten.

11. A device according to claim 9, wherein the conductive tracks are made of aluminium.

12. A device according to claim 9, wherein the conductive tracks are made of copper.

13. A device according to claim 1, wherein conductive tracks are connected to the heater that taper towards the heater.

14. A device according to claim 1, wherein conductive tracks are connected to the heater that taper away from the heater.

15. A device according to claim 1, wherein conductive tracks are connected to the heater that have parts made of two different materials.

16. A device according to claim 15, wherein the conductive tracks have an inner part made of a semiconductor and an outer part made of a metal.

17. A device according to claim 16, wherein the semiconductor is single crystal silicon.

18. A device according to claim 16, wherein the semiconductor is polysilicon.

19. A device according to claim 16, wherein the metal is aluminium.

20. A device according to claim 16, wherein the metal is tungsten.

21. A device according to claim 16, wherein the metal is copper.

22. A device according to claim 1, which incorporates a heat spreading plate.

23. A device according to claim 1, wherein the heater surrounds the spreading plate.

24. A device according to claim 1, which incorporates a sensor for providing an electrical output indicative of gas reaction with the gas-sensitive layer.

25. A device according to claim 1, wherein the sensing area incorporates temperature sensing means.

26. A device according to claim 1, wherein the material of the substrate has been removed in the sensing area to leave the membrane incorporating the sensing area.

27. A device according to claim 1, which is a resistive gas-sensing device.

28. A device according to claim 1, which is a calorimetric gas-sensing device.

* * * * *